United States Patent [19]

Hansen et al.

[11] 4,299,815

[45] Nov. 10, 1981

[54] CARCINOEMBRYONIC ANTIGEN DETERMINATION

[75] Inventors: Hans J. Hansen, Allendale; Alfred D. Myl, Elmwood Park; Jacques P. Vandevoorde, West Caldwell, all of N.J.

[73] Assignee: Hoffmann-La Roche Inc., Nutley, N.J.

[21] Appl. No.: 120,017

[22] Filed: Feb. 8, 1980

[51] Int. Cl.³ .................. G01N 33/48; G01T 1/00; G01N 33/54

[52] U.S. Cl. ..................... 424/1; 23/230 B; 424/12; 435/7

[58] Field of Search ............... 424/1, 12; 23/230 B; 435/7

[56] References Cited

U.S. PATENT DOCUMENTS

| | | | |
|---|---|---|---|
| 3,663,684 | 5/1972 | Freedman et al. | 424/1 |
| 3,697,638 | 10/1972 | Hansen | 424/1 |
| 3,867,363 | 2/1975 | Hansen | 424/1 |
| 4,098,876 | 7/1978 | Piasio et al. | 424/1 |
| 4,140,753 | 2/1979 | Edgington et al. | 424/1 |
| 4,180,499 | 12/1979 | Hansen | 260/112 R |

*Primary Examiner*—Benjamin R. Padgett
*Assistant Examiner*—Christine M. Nucker
*Attorney, Agent, or Firm*—Jon S. Saxe; George M. Gould; John J. Maitner

[57] ABSTRACT

An improved process for the determination of carcinoembryonic antigen in a sample of serum or plasma is disclosed. The improved process, in essence, comprises negating potentially interfering substances in the sample by diluting the sample with water and heating to a temperature below that which, at the ionic strength and pH of the sample, would cause coagulation of the proteins present and carrying out a radioimmunoassay for carcinoembryonic antigen on said sample.

13 Claims, No Drawings

CARCINOEMBRYONIC ANTIGEN DETERMINATION

BACKGROUND OF THE INVENTION AND STATEMENT OF PRIOR ART

The determination of carcinoembryonic antigen (hereinafter CEA) is well documented in the art. It is likewise well established that certain non-specific interfering substances present in the sample to be tested must be substantially removed or neutralized in some manner in order for the determination to be accurate and sensitive.

There are a number of procedures known in the art by which potentially interfering substances present in a sample of biological fluid, e.g., serum or plasma, can be removed or neutralized before testing for CEA. It is clearly an advantage to simplify the manipulations required to remove such interfering substances in a given assay in terms of time, cost and relative ease in conducting the test.

More particularly, in the determination of CEA as taught in Freedman et al., U.S. Pat. No. 3,663,684, tissue containing CEA is initially treated with a glycoprotein solvent in which CEA is soluble. Examples of such solvents include perchloric acid, trichloroacetic acid, phosphotungstic acid, and the like. The purpose of treating the tissue with the glycoprotein solvent is to remove precipitable normal proteins and interfering antigenic materials. The precipitated interfering protein material is thereafter removed from the sample by centrifugation.

More recently, Hirai, Cancer Research 37, 2267-2274, July 1977, and Kim, et al., Clinical Chemistry 25, No. 5, 773-776, 1979, have reported a method of determining CEA utilizing a preparative heat treatment in place of the extraction with a glycoprotein solvent, such as perchloric acid. The latter publication describes this method of preparation of sample to remove interfering substances as buffering the sample to a pH of 4.8 to 5.0 with acetate buffer and heating it to between 70° C. and 80° C. for from 10 to 20 minutes. This heat treatment in the presence of a high ionic strength buffer at acid pH, e.g., heat denatures the interfering proteins which coagulate. It is, therefore, essential that the sample be centrifuged to remove the coagulated material. This procedure is disadvantageous in that CEA present in the sample may become entrapped in the coagulated material and thereby removed from the sample to be tested, thereby detracting from the accuracy of the subsequent determination.

In accordance with the present invention, a method is disclosed for the preparation of a sample of human serum or plasma for assay for determination of CEA which is more rapid, easier and less expensive than the preparative methods known in the art and which is advantageous in that the sample need not be centrifuged.

DETAILED DESCRIPTION OF THE INVENTION

In accordance with the present invention, a method of preparing samples of human serum or plasma for assay for carcinoembryonic antigen (CEA), is described which is rapid, convenient and less expensive than methods used heretofore. The method of the present invention comprises diluting the sample with water, heating the sample to temperature below that which, at the ionic strength and pH of the sample, will cause the protein present therein to coagulate, i.e., a temperature of from about 85° to about 105° C., preferably about 95° C., for a relatively short time. Within the scope of the present invention an improved assay for CEA incorporated the herein disclosed preparative methodology.

In the heating step of the preparative methodology of the present invention, a sample of serum or plasma from a patient to be tested is heated for from about 3 to about 30 minutes, preferably for from about 5 to about 10 minutes. The length of time the sample is maintained at the above temperatures is not particularly critical to the practice of the present invention. It is only necessary that the sample be heated to the above-specified temperature and preferably maintained for a short period of time, e.g. 5 to 10 minutes. Therefore, the time of heating given herein is given for purposes of illustration, it being necessary only that the sample be heated to the desired temperature and maintained for a short time to assure that all of the sample has reached the desired temperature. As previously stated, in accordance with the method of the present invention, the sample must be heated to a temperature below that which, at low ionic strength and neutral to slightly alkaline pH, will cause any of the proteins therein to coagulate.

The dilution of the test sample with water is necessary to keep the ionic strength of the sample low, i.e., at most, an ionic strength one-eighth that of normal physiological ionic strength. Although tap water could be utilized for the dilution step, distilled or deionized water is preferred. Generally, a dilution of from about 1:8 to about 1:50 is utilized with a preferred dilution being about 1:16. The sample, thus diluted, will be of low ionic strength and have a neutral or slightly alkaline pH, i.e., a pH from about 7 to about 9. In the dilution range given above, it has been found that it is usually not necessary to dilute the sample with water containing a buffer. In order to maximize the sensitivity of the assay, however, it may be preferable to add a buffer to the water utilized to dilute the sample to assure that the pH is maintained at a slightly alkaline level. Wherein a buffer would be utilized in diluting the sample, conventional alkaline buffers, such as, for example, a tris (hydroxymethyl)amino methane buffer would be suitable. A sufficient amount of the buffer would be utilized to assure that the pH of the sample is slightly alkaline, i.e., a pH of from about 7.5 to about 9.0.

In addition to the avoidance of the need to centrifuge the sample as is required with the prior art heat treatment, the preparatory method of the present invention is advantageous in that it facilitates the assay of smaller quantities of sample, i.e., about 100 μl., than has heretofore been considered practical. For example, the present commercial radioimmunoassay for CEA utilizes an 0.5 ml. sample. The reduction in sample size for CEA in comparison with known assays is realized without a significant loss in the sensitivity of the assay. Further, the significant savings in time and cost resulting from the use of the preparatory method of the present invention make possible assays for CEA on a relatively large scale, e.g., for mass screening. A complete assay for CEA incorporating the preparatory method of the present invention can be conducted in about four hours. This represents a significant improvement over the commercial CEA assay utilizing dialysis which must be run overnight. In addition, the CEA assay in accordance with the present invention affords a significant advantage in the range of sensitivity of the assay over present commercial assays as will be discussed hereinafter.

The preparatory method of the present invention, in essence comprises diluting the sample of plasma or serum to a dilution of from about 1:8 to about 1:50, preferably about 1:16, and heating the diluted sample to a temperature below that which would cause coagulation of the proteins therein, i.e., a temperature of from about 85° to about 105° C., preferably about 95° C. The exact principle by which this method negates interfering problems in the sample which, heretofore it was thought must be physically removed therefrom, is not known.

The sample preparatorily treated in accordance with the present invention is allowed to return to ambient temperature and thereafter subject to the appropriate assay for CEA. The choice of a particular type of immunoassay for CEA to be utilized is not critical to the preparatory method of the invention. Generally, a radioimmunoassay or enzyme immunoassay is preferred with a radioimmunoassay being particularly preferred.

In general, a determination of CEA in accordance with the present invention comprises:
 (a) preparing a sample of serum or plasma from a patient as disclosed herein to neutralize potentially interfering materials;
 (b) adding an excess of an antibody to CEA to the samples to be tested and incubating for a predetermined time;
 (c) adding labeled CEA to the samples and incubating for a predetermined time;
 (d) adding to the mixture of (b) and (c) an insolubilizing agent thereby forming a solid phase containing antibody-bound CEA and a liquid phase containing unbound CEA;
 (e) separating said solid and liquid phases;
 (f) determining the amount of said label in either said solid or said liquid phase; and
 (g) determining the amount of CEA present in the sample by comparison to a standard.

In the above determination the term "neutralize" interfering materials is utilized. It will, of course, be appreciated that such term is intended to mean treatment in accordance with the present invention, as well as the various prior art procedures whereby such materials are physically removed from the sample, since the effect in each instance is the same. Therefore, the term, in essence, means that the immunological effect of such interfering materials is negated.

As previously stated, the label utilized to label the CEA in the aforementioned determination may be any immunologically compatible labeling substance amenable to quantitative determination, such as, for example, a radioisotope, an enzyme, a fluorescent or chemiluminescent substance and the like. Enzyme and radioisotope labels are preferred with the latter being particularly preferred. Among the radioisotopes conventionally utilized for radioimmunoassays, the isotopes of iodine are preferred with iodine-125 being particularly preferred.

The insolubilizing agent utilized to form a solid phase containing antibody-bound CEA and a liquid phase containing unbound CEA can be any material conventionally recognized in the art for such purpose. For example, certain aliphatic alcohols, ion exchange resins and inorganic salts as well as antibodies to the CEA antibody will cause the formation of a protein precipate which contains antibody-bound CEA. A preferred insolubilizing agent is second antibody, i.e., antibody to the CEA antibody, in immobilized, i.e., insolubilized, form.

With regard to the immobilization of second antibody discussed above, any of the numerous techniques recognized in the art of insolubilization of an immunological component, such as particles of various sizes, beads, sticks, or a strip of support medium, may be utilized. It will be appreciated that, wherein a particular insolubilization material is polymeric in nature, e.g., a styrene polymer or copolymer, it may be utilized in more than one of the above-given forms, depending on its properties. A particularly preferred material for immobilization of the second antibody is unsintered poly(vinylidene fluoride) which may be utilized, for example, in finely particulate form or as a film. The antibody may be physically adsorbed into the immobilizing material or chemically bound thereto by methods conventional in the art.

The particular proportions, incubation times and temperatures utilized for a given determination of CEA are considered to be within the skill of the art given the large body of knowledge published with regard to CEA. With regard to the determination of CEA utilizing the novel preparative methodology of the present invention in a radioimmunoassay, it has been found that it is possible to utilize significantly smaller volumes of reagents and sample in comparison to the commercial CEA determination without appreciable loss in sensitivity. This facilitates the use of smaller reaction tubes, reading equipment and the like. An additional advantage is that, because of an approximately five-fold reduction in the amount of antibody to CEA utilized in the procedure for determining CEA according to the subject invention in comparison to the commercial CEA radioimmunoassay, antisera to CEA need be standardized less frequently resulting in a considerable saving in time and expense. The assay for CEA in accordance with the present invention is further advantageous over the present commercial CEA radioimmunoassay in that the latter is accurate up to approximately 20 ng/ml. of CEA. In the situation wherein chemotherapy is being monitored and higher amounts of CEA must be determined, it would be necessary to utilize a different type of assay, i.e., a direct type assay to monitor such higher amounts. This latter type assay would be utilized to accurately determine CEA concentrations beginning at a minimum of about 40 ng/ml., thus leaving a gap of approximately 20 ng/ml. between it and the commercial radioimmunoassay for CEA. The determination of CEA in accordance with the present invention facilitates accurate readings for CEA up to a concentration of about 100 ng/ml., thus filling the aforementioned gap and affording a substantial saving in time and cost to the patient, since there is no need for a second assay to determine CEA concentrations substantially in excess of 20 ng/ml.

It has been found in accordance with the present invention that only about 0.1 ml. of sample to be tested can be utilized in conducting the determination and that about 5 μl. of CEA antiserum would be added to both the sample and standard. Preferred incubations for reaction of the antiserum and the subsequent reaction with labeled CEA are from about 80 minutes to about two hours with 90 minutes being particularly preferred. These incubations are carried out at a temperature of about 45° C. Wherein an enzyme label is utilized, adjustment in the incubation time and particularly the temperature may be required to prevent inactivation of the enzyme, if it is labile at the temperatures suggested herein. Wherein immobilized second antibody is utilized as the insolubilizing agent, the samples are preferably incubated at ambient temperature for from about 15 to 30 minutes preferably about 20 minutes. The determination of CEA in the sample is made by comparison to a standard curve as is conventional in the art. Reading of the label concentration is likewise carried out by conventional means depending on the type of label, e.g., by use of a gamma scintillation spectrometer where a radionuclide label is utilized.

The following Examples further illustrate the invention. Unless otherwise indicated, all temperatures are in degrees Centigrade.

EXAMPLE 1

The commercial determination for CEA was carried out as follows:

Samples (0.5 ml.) of plasma (in duplicate) from suspected colon cancer patients were extracted with 2.5 ml. of cold 1.2 molar perchloric acid by mixing in a vortex type mixer for 30 seconds and then centrifuging at 1000 x gravity for 20 minutes. The supernatants were collected and transferred to dialysis bags and dialyzed against deionized water changing the water three times with a minimum of three hours between changes. A final dialysis was carried out utilizing an ammonium acetate buffer, pH about 6.5. After dialysis, the contents of the dialysis bags were transferred to test tubes and 25 µl. of commercial CEA antiserum added to each with mixing in a vortex mixer. The tubes were incubated at 45° for 30 minutes. To each tube was added 25 µl. $^{125}$I-CEA with mixing and the tubes again incubated at 45° for 30 minutes. A total of 2.5 ml. of zirconyl phosphate gel, pH 6.25, was added to each tube and the contents centrifuged at 1000 x gravity for 5 minutes. The supernatants were removed and 5 ml. of ammonium acetate buffer, pH 6.25, were added with mixing. The contents of the tubes were again centrifuged as before and the supernatants removed. The amount of bound $^{125}$I-CEA in the remaining gel was determined by counting with a gamma scintillation spectrometer for one minute.

A standard inhibition curve was prepared as follows:

To pairs of test tubes was added 5.0 ml. of a 1 to 10 dilution of EDTA buffer (pH 6.5) with deionized water. To each pair of tubes was added CEA standard dose, i.e., 0, 10, 25, 50, and 100 µl. equivalent to 0, 1.25, 3.125, 6.25 and 12.5 ng/ml. of CEA activity and the contents mixed with a vortex-type mixer. The tubes were then treated with antisera to CEA and $^{125}$I-CEA as above. The readings were taken and a curve established for comparison of the readings obtained with the samples of patient plasma.

EXAMPLE 2

A determination of CEA in accordance with the present invention was carried out as follows:

Samples (0.1 ml.) of plasma were diluted with 1.5 ml. of deionized water and mixed on a vortex-type mixer. The tubes were placed in a water bath at 95° for ten minutes, after which they were removed and allowed to cool to room temperature. To each tube was added 5 µl. of commercial CEA antiserum with mixing in a vortex mixer. The tubes were incubated at 45° for 90 minutes. To each tube was added 25 µl. of $^{125}$I-CEA with mixing and the tubes again incubated for 90 minutes at 45°. To each tube was added 500 µl. of an aqueous suspension of antibody against the CEA antiserum insolubilized by adsorption on particles of poly(vinylidene fluoride). The tubes were again vortexed and incubated for 20 minutes at room temperature. The samples were then centrifuged at 1000 xg for 10 minutes. The supernatants were decanted and the tubes counted in a gamma scintillation spectrometer.

A standard inhibition curve was prepared as follows:

To pairs of test tubes was added 0.1 ml. of reconstituted lyophilized human plasma which was diluted with 1.5 ml. of deionized water. The contents of the tubes were mixed on a vortex-type mixer and incubated at 95° for 10 minutes. To each pair of tubes was added CEA standard dose, i.e., 0, 5, 10, 25, 50, and 100 µl. equivalent to 0, 0.625, 1.25, 3.125, 6.25 and 12.5 ng/ml. of CEA activity and the contents mixed on a vortex-type mixer. The tubes were treated with antisera to CEA, $^{125}$I-CEA and insolubilized second antibody as above. The readings were taken and a curve established for comparison of the readings obtained with the samples of patient plasma.

In Table I, the results for the samples prepared in accordance with the commercial dialysis method of Example 1 and the method of the subject invention, Example 2, were compared.

TABLE I

| Sample No. | Example 1 | Example 2 |
|---|---|---|
| 1 | 0.8 | 1.8 |
| 2 | 0.9 | 1.0 |
| 3 | 4.1 | 4.4 |
| 4 | 3.7 | 5.6 |
| 5 | 10.5 | 11.4 |
| 6 | 1.5 | 1.4 |
| 7 | 1.0 | 0.0 |
| 8 | 3.3 | 3.4 |
| 9 | 7.9 | 10.1 |
| 10 | 2.0 | 3.8 |
| 11 | 0.5 | 1.9 |
| 12 | 4.8 | 4.4 |
| 13 | 6.9 | 5.3 |
| 14 | 1.5 | 0.4 |
| 15 | 1.4 | 1.9 |
| 16 | 3.2 | 4.3 |
| 17 | 10.5 | 11.2 |
| 18 | 1.9 | 1.2 |
| 19 | 4.8 | 4.7 |
| 20 | 3.2 | 3.6 |
| 21 | 11.6 | 11.9 |

The results given in Table I clearly show that, in concentrations of CEA up to 20 ng/ml., the methods of examples 1 and 2 demonstrate good correlation of results, coefficient of correlation equals 0.963, slope equals 1.03.

EXAMPLE 3

In samples assayed in accordance with the procedure of Example 1 wherein the results indicated that the sample contained CEA concentrations in excess of 20 ng/ml., the commercial procedure for determining such concentrations was carried out as follows:

Samples (50 µl) of plasma were added to test tubes containing 5 ml. ammonium acetate buffer, 0.01 M acetate, pH 6.8. To each tube was added 25 µl of CEA antiserum and the contents mixed on a vortex-type mixer. The tubes were incubated at 45° for 30 minutes. To each tube was then added 25 µl. $^{125}$I-CEA and the tubes were again incubated at 45° for 30 minutes. A total of 2.5 ml. of zirconyl phosphate gel, pH 6.25, was added to each tube and the contents centrifuged at 1000 x gravity for 5 minutes. The supernatants were removed and 5 ml. of ammonium acetate buffer, pH 6.25, were added with mixing. The contents of the tubes were again centrifuged as before and the supernatants removed. The amount of bound $^{125}$I-CEA in the remaining gel was determined by counting with a gamma scintillation spectrometer for one minute.

A standard inhibition curve was prepared as follows. To each of pairs of test tubes was added 5.0 of 0.01 M acetate buffer, pH 6.8. To each tube was added 50 μl of normal human plasma and the contents thoroughly mixed. To each pair of tubes was added CEA standard dose, i.e., 0, 10, 25, 50, and 100 μl. equivalent to 0, 1.25, 3.125, 6.25 and 12.5 ng/ml. of CEA activity and the contents mixed with a vortex-type mixer. The tubes were then treated with antisera to CEA and $^{125}$I-CEA as above. The readings were taken and a curve established for comparison of the readings obtained with the samples of patient plasma.

The same samples were analyzed in accordance with the procedure of the method of the present invention, Example 2. A comparison of the results is shown in Table II.

TABLE II

| Sample No. | Example 2 | Example 3 |
|---|---|---|
| 1 | 18.5 | 30.7 |
| 2 | 49.1 | 95.4 |
| 3 | 32.0 | 67.5 |
| 4 | 25.0 | 54.1 |
| 5 | 25.3 | 72.1 |
| 6 | 23.8 | 56.9 |
| 7 | 32.8 | 63.9 |
| 8 | 30.4 | 49.8 |
| 9 | 37.9 | 85.2 |
| 10 | 23.3 | 43.6 |
| 11 | 26.5 | 41.7 |
| 12 | 47.5 | 51.5 |
| 13 | 34.7 | 47.1 |
| 14 | 17.6 | 40.6 |
| 15 | 29.1 | 68.5 |
| 16 | 23.5 | 36.1 |
| 17 | 25.7 | 41.4 |
| 18 | 19.9 | 26.3 |
| 19 | 86.4 | 67.5 |
| 20 | 33.1 | 68.2 |
| 21 | 27.6 | 67.1 |
| 22 | 30.2 | 59.6 |
| 23 | 26.1 | 72.5 |
| 24 | 29.8 | 59.0 |
| 25 | 28.2 | 55.5 |
| 26 | 17.8 | 36.7 |
| 27 | 20.6 | 38.6 |
| 28 | 91.5 | 91.8 |

The results given in Table II show that the method of the present invention permits accurate determination of concentrations of CEA in excess of 20 ng/ml. Tests conducted by diluting samples tested in this Example to achieve a concentration of CEA below 20 ng/ml. and assaying such diluted samples in accordance with the method of Example 1 demonstrated that the method of the present invention provides a more accurate determination of elevated CEA concentrations than the commercial procedure described in this example.

We claim:

1. A method of determining the concentration of carcinoembryonic antigen in a sample of serum or plasma from a human which comprises:
   (a) adding sufficient water to said sample to dilute it to a dilution of from about 1:8 to about 1:50,
   (b) heating said diluted sample to a temperature below that which will cause the protein present in said sample to coagulate for a period of from about 3 to about 30 minutes, thus neutralizing materials in said sample which would interfere with said determination;
   (c) adding an excess of an antibody to CEA to said sample and incubating for a predetermined time;
   (d) adding to said sample an amount of carcinoembryonic antigen labeled with a labeling substance capable of being quantitatively determined at least sufficient to react with the amount of antibody added in step (c) and incubating for a predetermined time;
   (e) adding to said sample an insolubilizing agent thus forming a solid phase containing antibody-bound CEA and a liquid phase containing unbound CEA;
   (f) separating said solid and liquid phases;
   (g) determining the amount of said labeling substance present in either said solid or said liquid phase; and
   (h) determining the amount of carcinoembryonic antigen present in said sample by comparison against a standard.

2. The method in accordance with claim 1 wherein said insolubilizing agent is an antibody against the antibody in step (c), said second antibody being in insolubilized form.

3. The method in accordance with claim 1 wherein said sample is diluted to a dilution of about 1:16.

4. The method in accordance with claim 1 wherein said diluted sample is heated for a period of from about 5 to about 10 minutes.

5. The method in accordance with claim 1 wherein said diluted sample is heated to a temperature between about 85° C. and about 105° C.

6. The method in accordance with claim 5 wherein said sample is heated to a temperature of about 95° C.

7. The method in accordance with claim 1 wherein said water utilized to dilute said sample contains a sufficient amount of a suitable buffer to buffer said sample to a pH of from about 7.5 to about 9.

8. The method in accordance with claim 1 wherein said labeling substance is a radioisotope.

9. The method in accordance with claim 8 wherein said radioisotope is a radioisotope of iodine.

10. The method in accordance with claim 9 wherein said radioisotope of iodine is iodine-125.

11. The method in accordance with claim 1 wherein said labeling substance is an enzyme.

12. The method in accordance with claim 1 wherein said labeling substance is a fluorescent substance.

13. The method in accordance with claim 1 wherein said labeling substance is a chemiluminescent substance.

* * * * *